US00PP17603P3

(12) United States Plant Patent
Michalik

(10) Patent No.: US PP17,603 P3
(45) Date of Patent: Apr. 17, 2007

(54) **VARIETY OF *GERANIUM* PLANT NAMED 'PENSYB'**

(50) Latin Name: *Pelargonium peltatum*
Varietal Denomination: Pensyb

(75) Inventor: Andrea Michalik, Dresden (DE)

(73) Assignee: Elsner pac Jungpflanzen, Dresden (DE)

( * ) Notice: Subject to any disclaimer, the term of this patent is extended or adjusted under 35 U.S.C. 154(b) by 1103 days.

(21) Appl. No.: 09/733,648

(22) Filed: Dec. 8, 2000

(65) Prior Publication Data

US 2002/0073471 P1 Jun. 13, 2002

(51) Int. Cl.
*A01H 5/00* (2006.01)

(52) U.S. Cl. ..... Plt./332
(58) Field of Classification Search ..... Plt./332, Plt./324
See application file for complete search history.

(56) References Cited

PUBLICATIONS

Licencing Agreement for 'Pensyb'; pp. 1–4; 1999.*

UPOVROM Citation for 'Pensyb' as per QZ PBR 980066; Jan. 14, 1998.*

UPOVROM Citation for 'Pensyb' as per PL PBR PBO0053; Feb. 22, 1999.*

UPOV ROM Citation for 'Pensyb' as per CZ PBR OPPH06596; Aug. 16, 1999.*

UPOVROM Citation for 'Pensyb' as per HU PLP9802251; Oct. 7, 1998.*

* cited by examiner

*Primary Examiner*—Kent Bell
(74) *Attorney, Agent, or Firm*—The Webb Law Firm

(57) ABSTRACT

A new and distinct zonal *geranium* plant with red colored flowers above medium green foliage. The plant is suitable for planting in small pots.

1 Drawing Sheet

Botanical classification: *Pelargonium peltatum.*
Varietal denomination: 'Pensyb'.

BACKGROUND OF THE INVENTION

The present invention comprises a new and distinct cultivar of *Pelargonium peltatum* known by the varietal name 'Pensyb'. The new variety was discovered in 1995 in a selective breeding program in Dresden, Germany. The new variety is the result of a cross between two unnamed, unpatented selections from breeding group 4K-57-35-II. The new variety was first asexually reproduced by cuttings in Dresden, Germany in 1995. The new variety has been trial and field tested and has been found to retain its distinctive characteristics and remain true to type through successive propagations. The new variety differs from its parental cultivars in having clear rosebud-type red colored flowers and more compact growth.

DESCRIPTION OF THE DRAWING

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions carried out in Dresden, Germany. Observations were made when the plants were 9 months old, grown in 45 cm diameter baskets. The color readings were taken outdoors in shadow during summer. Color references are primarily to The R.H.S. Colour Chart of The Royal Horticultural Society of London.

PLANT

Form: Hanging.
Height from media surface to top of foliage: 25–40 cm.
Height from media surface to top of umbel: 25–40 cm.
Width (spread): 35 cm.
Growth: High degree of branching.
Strength: Does not require artificial support.
Response time: 4 weeks.
Leaves:
- *Size.*—4–5 cm long; 5–6 cm wide.
- *Shape.*—Overall: Ivy-shaped. Base: Cordate. Apex: Pointed.
- *Margin.*—Entire.
- *Texture.*—Pubescent.
- *Color.*—Upper surface: 136B with a 146A zone. Lower surface: 138B.
- *Ribs and veins.*—Venation: Net-like. Color: 146B.

Petioles:
- *Color.*—146B.
- *Length.*—2–3 cm.
- *Diameter.*—2.0–3.0 mm.

Stem/branches:
- *Color.*—147B.
- *Internode length.*—1–2 cm.
- *Lateral branch length.*—10–15 cm.

THE BUD

Shape when just showing color:
- *Overall.*—Spherical.
- *Individual bud.*—Elliptical.

Color: Green Group 138A.

Size when just showing color:
*Umbel.*—5–6 cm across.
*Individual bud.*—0.7 long; 0.7–1 cm wide.

INFLORESCENCE

Quantity per plant: 60–70 per season.
Blooming habit: Double; early flowering; flowers during frost free season.
Borne: Umbel; flowers on pedicel; pedicel on peduncle.
Umbel: 6–8 cm across; 3–4 cm deep.
Flowers:
*Number of flowers.*—7–9.
*Form.*—Round.
*Number of petals.*—17–20.
*Size.*—3–3.5 cm across; 1–1.5 cm deep.
*Petals.*—Size: 1.5 cm long; 1 cm wide. Color: Upper surface: Red Group 53B. Lower surface: Red Group 43C. Base: Pointed. Margin: Entire.
*Shape.*—Overall: Round-elliptical. Apex: Round. Base: Narrow.
*Sepals.*—Quantity per flower: 5. Color: Upper surface: Green Group 143B. Lower surface: Green Group 143B. Shape: Overall: Elliptical. Apex: Pointed. Base: Blunt. Margin: Entire. Size: 1.3 cm×0.3 cm.
*Texture and appearance.*—Velvety.
*Tonality from a distance.*—Rose-like impression of the flower buds.
Petaloids:
*Quantity.*—12–15.
*Shape.*—Round; irregular.
*Color.*—Upper surface: 53B. Lower surface: 43C.
Pedicel:
*Length.*—1.0–1.5 cm.
*Color.*—Green Group 137C.
Peduncle:
*Length.*—7–9 cm.
*Color.*—Green Group 141C.
Disease/pest resistance: No susceptibility to diseases or pests has been noted to date.
Lasting quality: Long-lasting; early flowering; an individual bloom lasts for 3 weeks on the plant.
Natural flowering season: Summer, frost free period.

REPRODUCTIVE ORGANS

Stamens:
*Anthers.*—3 mm long.
*Filaments.*—Length: 0.5 cm maximum. Color: Pink.
*Pollen.*—Yellow; scant.
Pistils:
*Number.*—One, five parted.
*Length.*—0.3–0.4 cm.
*Stigma.*—Pink.
*Style.*—0.8 cm long.
*Color.*—Greenish.
Ovaries: Superior; some pubescence; greenish; 0.4 cm long.
Fruit: Not present.

GENERAL CHARACTERISTICS

1. Very compact.
2. Very early flowering.
3. Rose bud type.
4. Ideal for small pots.
5. Stable flower color under sun.

I claim:

1. A new and distinct variety of *geranium* plant substantially as shown and described.

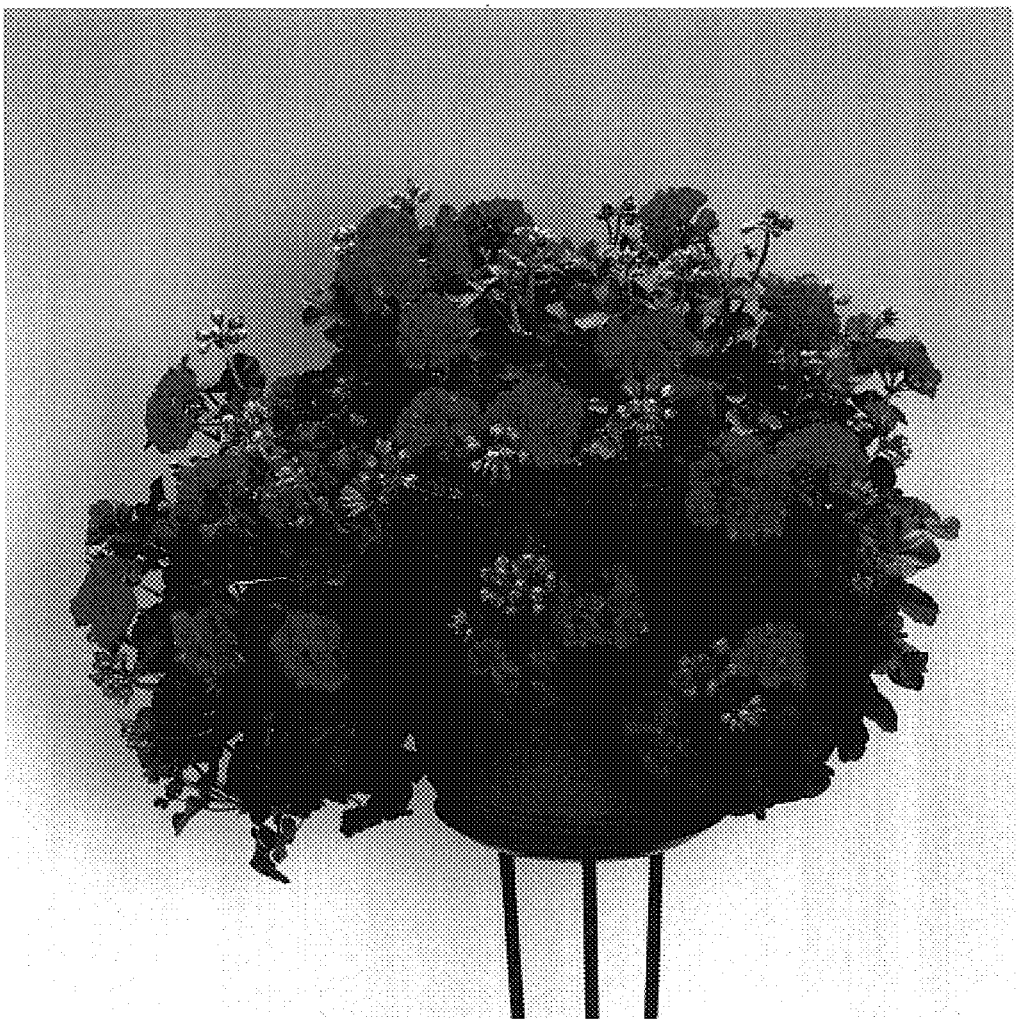

* * * * *